United States Patent [19]

Bristow

[11] Patent Number: 5,998,458

[45] Date of Patent: Dec. 7, 1999

[54] METHOD OF TREATING HEART FAILURE

[75] Inventor: Michael R. Bristow, Greenwood Village, Colo.

[73] Assignee: University Technology Corporation, Boulder, Colo.

[21] Appl. No.: 09/100,497

[22] Filed: Jun. 19, 1998

Related U.S. Application Data

[60] Provisional application No. 60/050,674, Jun. 25, 1997.

[51] Int. Cl.$^6$ ........................ A61K 31/415; A61K 31/135
[52] U.S. Cl. ............................. 514/392; 514/651
[58] Field of Search ..................... 514/392, 651

[56] References Cited

U.S. PATENT DOCUMENTS

| | | | |
|---|---|---|---|
| 3,873,600 | 3/1975 | Brandstrom et al. | 260/471 |
| 4,405,635 | 9/1983 | Schnettler et al. | 424/273 |

OTHER PUBLICATIONS

Baim et al., *N Engl J Med*, 309:748–56 (1983).
Bristow et al., *Coronary Artery Disease*, 5(2):112–118 (1994).
Cowley et al, *Br Heart J*, 72:226–30 (1994).
DiBianco et al, *N Engl J Med*, 320:677–83 (1989).
Feldman et al., *N. Engl. J. Med.*, 329:149–155 (1993).
Galie et al., *Cardiovasc Drugs Ther.*, 7:337–347 (1993).
Gilbert et al., *Clin Res.*, 40:259A (1992).
Gilbert et al., *Am. J. Cardiol.*, 60:57C–62C (1987).
Kelly and Smith, in *Heart Disease: A Textbook of Cardiovascular Medicine*, Chapter 16 at p. 488 (5th ed., Braunwald ed., 1997).
Kubo et al., *Circulation*, 85:942–949 (1992).
Lee et al., *J. Thorac. Cardiovasc. Surg.*, 102:246–258 (1991).
Massie, *Circulation*, 88:492–501 (1993).
The Consensus Trail Study Group—Results of the Cooperative North Scandinavian Enalapril Survival Study, *N. Engl. J. Med.*, 316:1429–35 (1987).
Packer et al, for the Promise Study Group, *N. Engl. J. Med.*, 325:1468–1475 (1991).
Packer et al, *N Engl J Med*, 325:1468–75 (1991).
Packer, *Lancet*, 340:92–95 (1992).
Schleman, for the Enoximone Study Group, *Circulation*, 84(suppl. II):II243 (1991).
Tiara et al., *Arzneim–Forsch Drug Res*, 34(I):3a (1984).
Uretsky et al., *Circulation*, 82:774–780 (1990).
Xamoterol in Severe Heat Failure Study Group, *Lancet*, 336:1–6 (1990).

*Primary Examiner*—Raymond Henley, III
*Attorney, Agent, or Firm*—Sheridan Ross P.C.

[57] ABSTRACT

The invention provides a method of treating heart failure. The method comprises administering a positive inotropic agent and a β-adrenergic receptor antagonist in a specific manner.

15 Claims, 3 Drawing Sheets

METHOD OF TREATING HEART FAILURE

Benefit of provisional application Ser. No. 60/050,674, filed Jun. 25, 1997, is hereby claimed.

FIELD OF THE INVENTION

The present invention relates to a method of treating heart failure. More particularly, the present invention relates to a method of treating heart failure using a positive inotrope and a β-adrenergic receptor antagonist.

BACKGROUND OF THE INVENTION

A variety of human diseases and conditions which are manifested by cardiac abnormalities or cardiac dysfunction can lead to heart failure. Heart failure is a pathophysiological condition in which the heart fails to pump blood at a rate commensurate with the requirements of the metabolizing tissues of the body. When the heart begins to fail, physiological mechanisms for modulating the function of the heart are utilized to increase heart rate and contractility.

Figure 1:
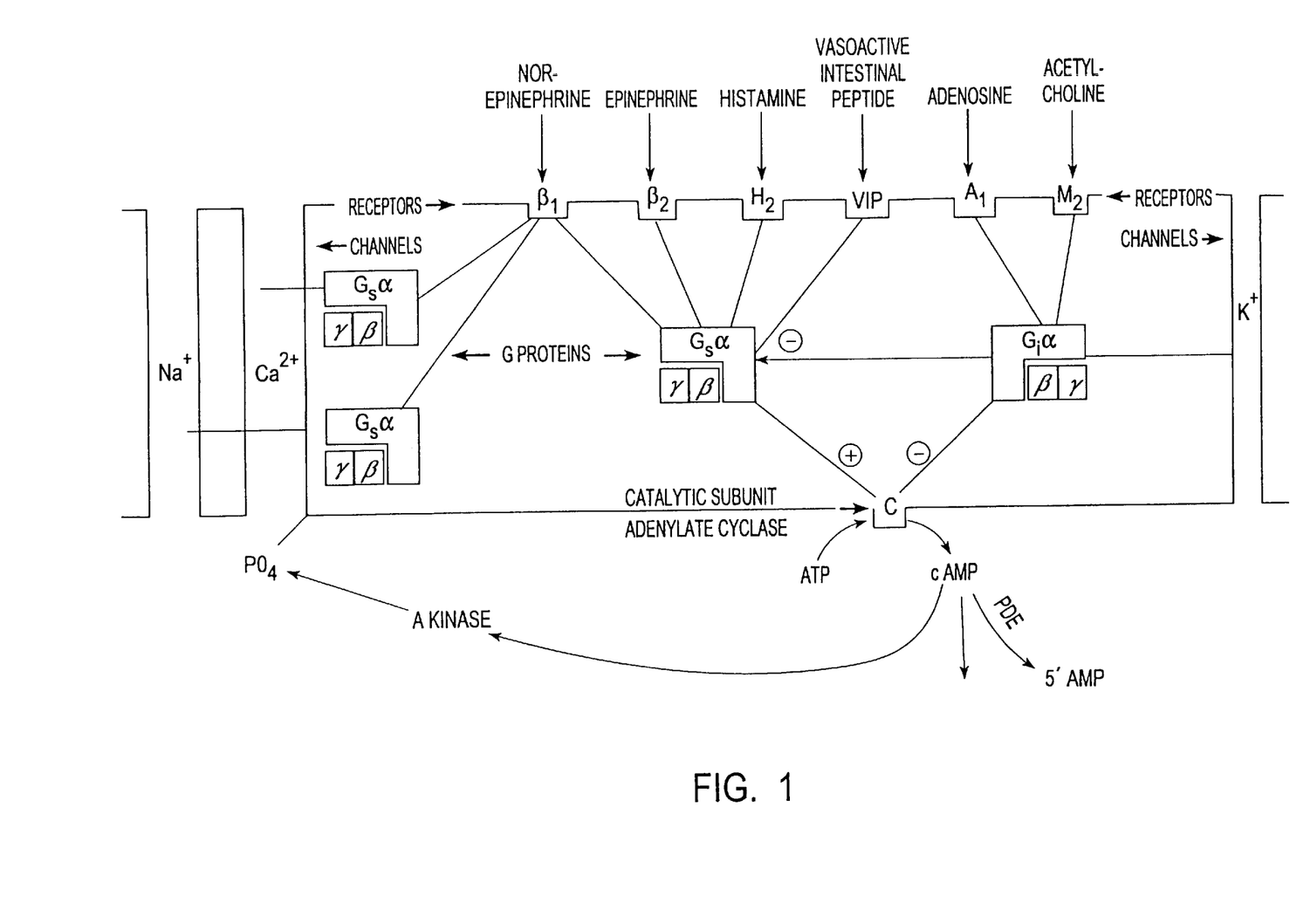
FIG. 1 is a diagram of a myocardial cell, showing signal transduction mechanisms involved in modulating contractile function. The diagram shows cyclic adenosine monophosphate (cAMP)-dependent and cAMP-independent pathways for various receptor agonists. G$_s$, stimulatory G protein; G$_i$, inhibitory G protein; C, adenylyl cyclase; PDE, phosphodiesterase. G$_s$ mediates the stimulation of adenylyl cyclase and, thereby, causes a rise in intracellular cAMP which, in turn, stimulates Ca$^{++}$ influx into the myocyte through Ca$^{++}$ channels in the sarcolemma and accelerates the uptake of Ca$^{++}$ by the sarcoplasmic reticulum. G$_i$ mediates the inhibition of adenylyl cyclase and has the opposite effect on the movement of Ca$^{++}$.

The most important of the mechanisms that are responsible for modulating cardiac function are the adrenergic pathways. In a normal heart, these pathways are largely responsible for allowing cardiac pumping performance to meet the circulatory demands of increased activity by rapidly increasing or decreasing cardiac function according to circulatory demands. The cellular actions of these pathways are mediated through a family of receptors, called adrenergic receptors. There are two β-adrenergic receptor subtypes, $\beta_1$ and $\beta_2$ which, when stimulated, initiate a G-protein coupled signaling cascade, resulting in immediate stimulation of pump performance. See FIG. 1.

When the heart begins to fail, adrenergic activity is stimulated by increased sympathetic nerve activity, presynaptic facilitation of norepinephrine release and eventually, decreased neuronal norepinephrine reuptake. Increased circulating epinephrine also stimulates cardiac β-adrenergic receptors, particularly in the initial phase of heart failure.

In heart failure, the immediate stimulation of pump performance by β-adrenergic mechanisms is subsequently aided by two additional means of stabilizing or increasing cardiac function. These are an increase in plasma volume, which in turn increases preload, and hypertrophy of the cardiac myocytes, which results in more contractile elements. The subcellular mechanisms mediating these additional cardiac functions include both the β-adrenergic receptor pathways and the $\alpha_1$-adrenergic receptor pathway, among other myocellular pathways.

In the failing ventricular myocardium, the exposure to elevated levels of cognate agonists causes the adrenergic receptors to undergo regulatory changes. In particular, the $\beta_1$-adrenergic receptor exhibits down-regulation or loss of receptor protein and may also be partially uncoupled from the signaling response. $\beta_2$-adrenergic receptors are not down-regulated, but are weakly uncoupled from the signaling response. The $\alpha_1$-adrenergic receptors are slightly up-regulated and are partially uncoupled from the signaling response. These changes in adrenergic receptor expression and signaling partially withdraw the cardiac myocyte from chronic stimulation, although some adrenergic function remains. The increased agonist exposure, however, continues to chronically stimulate the remaining adrenergic signaling function, resulting in the compromise of the modulatory effects of the adrenergic system. Therefore, the prime functional capabilities of the adrenergic system, to rapidly and substantially increase or decrease cardiac function according to demand, are compromised, while the adverse effects of chronic stimulation of cardiac function remain.

Numerous compounds have been identified and used to inhibit the functions of the β-adrenergic receptors, and thus, eliminate the adverse effects of chronic myocardial stimulation through the adrenergic pathways. These compounds, often called β-adrenergic receptor antagonists, β-adrenergic antagonists or β-blockers, interact with the β-adrenergic receptors and thereby inhibit or prevent cellular signaling by the endogenous agonists. One β-adrenergic antagonist can differ from another in a variety of ways, including by receptor subtype specificity, effect on expression of the adrenergic receptor, and effect on adrenergic receptor signaling.

Although β-adrenergic antagonists are important therapeutic tools for use in patients experiencing heart failure, these drugs often cause adverse side effects, such as bradycardia, myocardial depression, dyspnea, easy fatigability, fluid retention and worsening of heart failure. The characteristics which contribute to the undesirable side effects of β-adrenergic antagonists are controversial and not well understood. See Kelly and Smith, in *Heart Disease: A Textbook Of Cardiovascular Medicine,* Chapter 16 at page 488 (5th ed., Braunwald ed., 1997).

Another therapy for heart failure that has been investigated is the use of positive inotropic agents. Positive inotropic agents strengthen heart muscle contractility, and they exert their effects through the second messengers of the signal transduction pathways involved in modulating contractile function (illustrated in FIG. 1). Table 1 lists the second messengers involved in mediating a positive inotropic response for various inotropic agents. As shown in Table 1, positive inotropic agents use only a limited number of second messengers to mediate their cellular effects, and some use more than one second messenger. Table 2 lists the three most commonly observed second messengers and their effects on important processes in the heart and vascular smooth muscle, including increases in the heart rate, contractility and vasodilation. As seen in Table 2, only the intracellular second messenger cyclic adenosine monophosphate (cAMP) is capable of producing vasodilation and a positive inotropic effect. Cyclic AMP also produces an increase in heart rate, a very counterproductive property for a heart failure medication. In addition, all positively inotropic second messengers carry an arrhythmogenic risk that is usually dose-related.

TABLE 1

Second messengers used by various classes of inotropic agents

| Class | Second messengers |
| --- | --- |
| β-adrenergic receptor agonists | Cyclic AMP, $Ca^{2+}$ ($G_s \rightarrow Ca^{2+}$ channel) |
| $Ca^{2+}$ channel agonists | $Ca^{2+}$ |
| $\alpha_1$-adrenergic receptor agonists | Inositol triphosphate/DAG |
| Phosphodiesterase inhibitors | Cyclic AMP |
| Quinolones | Cyclic AMP, $?Ca^{2+}$ |
| Calcium sensitizers | $Ca^{2+}$, cyclic AMP |
| Cardiac glycosides | $Ca^{2+}$ |
| $Na^+$-channel agonists | $Ca^{2+}$ |

$G_s$, stimulatory G protein;
DAG, diacylglycerol;
AMP, adenosine monophosphate.

TABLE 2

Effect of second messengers on cardiovascular responses

| Second messenger | Heart rate | Cardiac contraction | Vascular response |
|---|---|---|---|
| Cyclic AMP | ↑↑ | ↑↑↑ | ↑↑↑ Dilation |
| IP$_3$/DAG | ←→ | ↑ | ↑↑ Constriction |
| Ca$^{2+}$ | ←→ | ↑↑ | ↑ Constriction |

IP$_3$, inositol triphosphate.

In the late 1970s and early 1980s the high degree of acceptance of the potential of positive inotropic agents by cardiologists and physicians was based on the intuitive belief that pharmacologic reversal of the intrinsic defects in myocardial contractility that characterize the failing heart could 'cure' the heart failure process. Since myocardial failure is characterized by a downward/rightward shift in the length-tension relationship, and positive inotropic agents shift this relationship upwards and to the left [Katz, *J. Am. Coll. Cardiol.*, 1, 42–51 (1983)], it seemed logical that this form of therapy would help the failing heart. Unfortunately, the concept was disproved by the xamoterol and Prospective Randomized Milrinone Survival Evaluation (PROMISE) trials which, respectively, demonstrated that a β-adrenergic receptor partial agonist (xamoterol) and a phosphodiesterase inhibitor (milrinone) increased mortality in subjects with heart failure. The Xamoterol in Severe Heart Failure Study Group, *Lancet*, 336, 1–6 (1990); Packer et al. for the PROMISE Study Group, *N. Engl. J. Med.*, 325, 1468–1475 (1991). The PROMISE trial ended the simple paradigm that positive inotropic therapy was the answer for ambulatory heart failure. In particular, influential opinion leaders in the heart failure field argued convincingly that any agent acting through a positive inotropic mechanism is likely to adversely affect the natural history of heart failure. Packer, *Lancet*, 340, 92–95 (1992).

In advanced, late-stage heart failure, β-adrenergic antagonists cannot be used, and often the only therapy available is intravenous positive inotropic agents. Although patients receiving intravenous inotropic agents usually feel better and improve hemodynamically for a short time, this treatment is expensive and has the potential to increase mortality. Other uses of positive inotropic therapy, including oral forms of positive inotropes, have been abandoned because of the above-mentioned increase in mortality.

It has been suggested that many of the adverse effects of positive inotropic agents could theoretically be ameliorated by simultaneous treatment with antagonists of neurohormonal activation such as an angiotensin converting enzyme (ACE) inhibitor or a β-adrenergic antagonist. Bristow and Lowes, *Coronary Artery Disease*, 5, 112–118 (1994). Actual results with ACE inhibitors have been mixed. Id. Two small, uncontrolled studies provide preliminary support for the use of a positive inotropic agent and a β-adrenergic receptor antagonist. Galie et al., *Cardiovasc. Drugs Ther.*, 7, 337–347 (1993); Gilbert et al., *Clin Res.*, 40, 259A (1992). However, the results of these studies are limited to the specific conditions used in the studies and cannot be extrapolated. Galie et al., *Cardiovasc. Drugs Ther., Vol.* 7, pp. 307–347 (1993). Also, larger, controlled studies are needed before this therapy can be considered useful. Bristow and Lowes, *Coronary Artery Disease*, 5, 112–118 (1994).

Chronic heart failure is a progressive disease syndrome which is associated with high degrees of morbidity and mortality despite medical therapy. Although heart transplantation can improve outcomes, a limited organ donor supply confines this treatment to fewer than 5% of subjects who could benefit from it. The effects of medical therapy on chronic heart failure are largely confined to modest effects (15–20% reductions in mortality) observed with ACE inhibitors in subjects with mild or moderate heart failure. Clearly, there exists a need for more effective pharmaceutical treatments for heart failure, especially for advanced, late-stage heart failure.

SUMMARY OF THE INVENTION

The invention provides a method of treating heart failure. The method comprises administering an effective amount of a positive inotropic agent to a patient suffering from heart failure until the patient is hemodynamically and clinically stable. Then, a β-adrenergic receptor antagonist is administered to the patient, beginning with a low dose which is gradually increased to an effective dose. The administration of effective doses of both the positive inotropic agent and the β-adrenergic receptor antagonist can be continued indefinitely. Preferably, however, after the positive inotropic agent and the β-adrenergic receptor antagonist have been administered in combination for at least two months, the dose of the positive inotropic agent is gradually reduced to the lowest possible dose that does not reduce the hemodynamic and clinical stability of the patient and is, most preferably, discontinued altogether.

DETAILED DESCRIPTION OF PRESENTLY PREFERRED EMBODIMENTS OF THE INVENTION

The invention provides a method of treating heart failure. Methods of diagnosing heart failure are well known in the art. See *Heart Disease: A Textbook Of Cardiovascular Medicine* (Braunwald ed., 5th ed., 1997). Symptoms associated with heart failure include shortness of breath, an inability to work or exercise, swollen feet and ankles, cyanosis respiratory congestion, and persistent cough. Reduced left (or right) ventricular ejection fraction, a measure of the heart's pumping efficiency, is the most reliable diagnostic indicator of heart failure. Echo-cardiography is commonly employed to detect other diagnostic indications of heart failure including increased chamber dimensions and wall thickness, various motion abnormalities, left ventricle dilation and hypertrophy.

The method of the invention has been found particularly useful for treating advanced, late-stage heart failure. Late-stage heart failure is characterized diagnostically by a severely reduced ventricular ejection fraction. It is characterized clinically as New York Heart Association [NYHA] Functional Class IV. Id. at 12. The patient is unable to carry on any physical activity without discomfort. Symptoms of cardiac insufficiency or of angina may be present even at rest. If any physical activity is undertaken, discomfort is increased. Other NYHA heart failure classifications include: NYHA Class I—asymptomatic; NYHA Class II—symptomatic with routine exertion; and NYHA Class III—symptomatic with less than routine exertion. Id.

Any positive inotropic agent may be used in the practice of the invention, except for cardiac glycosides and β-adrenergic receptor agonists. The β-agonists would compete with the β-adrenergic receptor antagonists used in the method of the invention. Moreover, in a multicenter trial, the partial β-agonist xamoterol was found to increase mortality by 148%. See Bristow and Lowes, *Coronary Artery Disease*, 5, 112–118 (1994). In contrast, the phosphodiesterase inhibitor milrinone produced only a 24% increase in mortality. Id.

Preferably the positive inotropic agent acts through the second messenger cAMP, since only cAMP produces vasodilation, as well as a positive inotropic effect (see Tables 1 and 2 above). However, although vasodilation is desirable, powerful vasodilation should be avoided.

The main problem with agents acting through cAMP is their positive chronotropic effects. An increase in the heart rate can be negatively correlated with effects on survival across several classes of drugs, including angiotensin converting enzyme (ACE) inhibitors, vesnarinone, milrinone, flosequinan, and prostacyclin. However, in the practice of the invention, the increase in heart rate is lessened or completely eliminated by the use of the β-adrenergic antagonist.

A weaker versus a more powerful inotropic agent is preferred. A comparison of the maximum inotropic responses obtained with seven different agents in isolated right ventricular trabeculae removed from non-failing and failing human hearts shows that the quinolinone compounds OPC-8490 and OPC-18790 and the quinoline flosequinan are weak inotropic agents, while the sodium-channel agonist BDF-9148 and the phosphodiesterase inhibitors enoximone and milrinone are moderately powerful, and the full, non-selective agonist isoproterenol gives the most powerful inotropic response. Bristow and Lowes, *Coronary Artery Disease*, 5, 112–118 (1994).

Effective dosage forms, modes of administration and dosage amounts of the positive inotropic agent, may be determined empirically, and making such determinations is within the skill of the art. It is understood by those skilled in the art that the dosage amount will vary with the activity of the particular agent employed, the severity of the heart failure, the route of administration, the rate of excretion, the duration of the treatment, the identity of any other drugs being administered to the patient, the age and size of the patient, and like factors well known in the medical art.

The lowest dose of the positive inotropic agent which is effective should be used. Lower doses of positive inotropic agents have been found to produce lower rates of mortality, as compared to higher doses. See Bristow and Lowes, *Coronary Artery Disease*, 5, 112–118 (1994); Gilbert et al., *Am. J. Cardiol.*, 60, 57C–62C (1987); Lee et al., *J. Thorac. Cardiovasc. Surg.*, 102, 246–258 (1991); Schleman, for the Enoximone Study Group, *Circulation*, 84 (suppl. II), II243 (1991); Uretsky et al., *Circulation*, 82, 774–780 (1990); Kubo et al., *Circulation*, 85, 942–949 (1992); Feldman et al., *N. Engl. J. Med.*, 329, 149–155 (1993). As used herein the "lowest effective dose" of an inotropic agent is the lowest dose effective in producing a beneficial therapeutic effect.

The inotropic therapy should, preferably, produce a minimal or no effect at rest, and then a more vigorous positive inotropic response during periods of increased demand, such as during exercise. Phosphodiesterase inhibitors are uniquely capable of this function, since the increased level of cAMP generated by these agents with increased adrenergic signaling during exercise will produce a greater inotropic effect. Therefore, at the right dose, the phosphodiesterase inhibitor will have little or no inotropic effect at rest, but a clear-cut effect on exercise. This function will be heightened by the concurrent β-adrenergic receptor blockade.

Suitable modes of administration of the positive inotropic agent can include, but are not limited to, oral, nasal, topical, transdermal, rectal, and parenteral routes. Preferred parenteral routes include, but are not limited to, subcutaneous, intradermal, intravenous, intramuscular and intraperitoneal routes.

Preferably, the positive inotropic agent is administered orally. As noted above, advanced, late-stage heart failure patients are often treated with intravenous positive inotropes, typically the β-agonist dobutamine. If a patient is on intravenous positive inotropic therapy, the patient is preferably gradually withdrawn from the intravenous inotrope as the dose of an oral inotrope according to the invention is gradually increased to the effective dose.

In the method of the present invention, the positive inotropic agent is administered to a patient suffering from heart failure until the patient is hemodynamically and clinically stable. The time for a patient to become hemodynamically and clinically stable is typically about 2–6 weeks. During this time, the positive inotropic agent and other heart failure medications, such as diuretics, ACE inhibitors, and digoxin, are adjusted to optimal levels as the patient is progressively physically rehabilitated.

Although there is no ideal positive inotrope, the positive inotrope is preferably a phosphodiesterase inhibitor. Phosphodiesterase inhibitors are moderate inotropes which, at the right dose, produce a minimal or no effect at rest and a more vigorous positive inotropic response during periods of increased demand, such as during exercise. Since they act solely through cAMP, they provide vasodilation as well as inotropic effects. Finally, to the extent that data is available, they give less increased mortality than other positive inotropes.

Most preferably, the positive inotropic agent is the phosphodiesterase inhibitor enoximone. A suggested daily dosage of enoximone is about 1–3 mg/kg/day, preferably administered in 3 or 4 divided doses. However, the total daily dosage of the agent will be determined by an attending physician within the scope of sound medical judgment.

In the method of the present invention, a β-adrenergic receptor antagonist is used to overcome the adverse effects of the positive inotropic agent. For instance, since cAMP production is lessened by removing nonrepinephrine from adrenergic receptors, the action of positive inotropes which depend on the production of cAMP to exert their effects will be decreased. Increased availability of cAMP should occur only intermittently when the β-blocker is outcompeted for the receptor by high cardiac adrenergic drive, that is, when the cardiac myocyte needs the inotropic support. Thus, it will be possible to reduce the overall adverse effects of adrenergic activation with a Unblocking agent and still make use of the inotropic property of a positive inotrope, particularly intermittently at times when neurotransmitter release is increased, for example, during exercise. In essence, the combination of a β-blocker and a positive inotrope provides a better hemodynamic profile and normalizes abnormal cardiac adrenergic neuroeffector mechanisms in heart failure.

As used herein, a "β-adrenergic receptor antagonist" is a compound which blocks, at least partially, an effect of the endogenous β-adrenergic receptor agonists (e.g., epinephrine and norepinephrine). Many β-adrenergic antagonists can also bind to and have a regulatory effect on alpha (α)-adrenergic receptors. Therefore, as used herein, β-adrenergic receptor antagonists include adrenergic receptor antagonists that can bind to α-, as well as β-adrenergic receptors.

The two β-adrenergic receptor subtypes, $\beta_1$ and $\beta_2$, are coupled by the stimulatory guanine nucleotide-binding protein ($G_s$) to the effector enzyme, adenylyl cyclase, on the cell surface membrane of myocardial cells. See FIG. 1. When an agonist binds to the $\beta_1$ or $\beta_2$ receptor, the a subunit of $G_s$ ($\alpha G_s$) increases its binding affinity for guanosine triphosphate (GTP), which then preferentially binds GTP over guanosine diphosphate (GDP). The $\alpha G_s$-GTP complex is a powerful stimulus for the activation of adenylyl cyclase, which generates cAMP from adenosine triphosphate (ATP). Cyclic AMP typically exerts its effect in a cell by activating cAMP-dependent protein kinase A (PKA), which in turn phosphorylates various target proteins, thereby regulating the activity of the target protein. Cyclic AMP exerts positive inotropic and chronotropic activity by increasing the flux of calcium through sarcolemmal slow $Ca^{2+}$ channels and increasing $Ca^{2+}$ uptake and release by the cytoplasmic reticulum. In addition, $\beta_1$-adrenergic receptors are coupled through $G_s$ to slow $Ca^{2+}$ channel influx by cAMP-independent pathways. Activation of these pathways leads to an increase in myosin ATPase activity, resulting in increased heart pump performance.

Unoccupied adrenergic receptors appear to possess a low level of intrinsic activity. In other words, a small percentage of the total adrenergic receptors on a cell exist, at a given time, in an active conformation that is in equilibrium with a more abundant, inactive conformation. Receptors in an active conformation initiate signal transduction even in the absence of agonists. Also, agonists bind to the active conformation of the receptor, stabilizing it and shifting the equilibrium toward the active signaling conformation.

Adrenergic receptor antagonists exert their effect through a variety of mechanisms. Some adrenergic receptor antagonists act as neutral antagonists. Neutral antagonists bind equally to the active and inactive conformations of a receptor. Neutral antagonists, therefore, have no effect on the intrinsic activity of an adrenergic receptor.

Another class of adrenergic receptor antagonists are negative antagonists, also called inverse agonists. Inverse agonists inhibit the intrinsic activity of the adrenergic receptor, presumably by binding preferentially to the inactive conformation, shifting the equilibrium toward the receptor conformation that does not initiate signaling.

Other adrenergic receptor antagonists exhibit a characteristic known as intrinsic sympathomimetic activity. Antagonists having intrinsic sympathomimetic activity are partial or weak agonists. They shift the adrenergic receptor moderately toward an active conformation, but their binding blocks the action of the more potent endogenous agonists.

Many adrenergic receptor antagonists are known (see, e.g., *Heart Disease: A Textbook Of Cardiovascular Medicine*, pages 486–488, 610–613 and 853 (5th ed., Braunwald ed., 1997)), and their tolerability can be evaluated as described below. Additional adrenergic receptor antagonists can be identified by a variety of methods well known in the art. For instance, to determine if a compound is a β adrenergic receptor antagonist, competitive binding experiments with $^{125}$I-iodocyanopindolol (ICYP), a compound which binds selectively to β adrenergic receptors, can be employed. Suitable conditions are described in Bristow et al., *Circulation*, 84, 1024–1039 (1991); Chidiac et al., *Molec. Pharmacol.*, 45, 490–99 (1994). Competitive binding experiments with an agonist can also be employed to identify antagonists (see definition of antagonists above). Binding to $\beta_1$ or $\beta_2$ adrenergic receptors can be differentiated in a number of ways, such as competitive binding experiments using known $\beta_1$- or $\beta_2$-specific ligands or, preferably, using recombinant cells transformed to express only $\beta_1$ or $\beta_2$ adrenergic receptors (see, e.g., Tate et al., *Eur. J. Biochem.*, 196, 357–361 (1991); Samama et al., *Molec. Pharmacol.*, 45, 390–94 (1994); Chidiac et al., *Molec. Pharmacol.*, 45, 490–99 (1994); Yoshikawa et al., *Eur. Heart J.*, 17 (Supp. B), 8–16 (1996)). Compounds binding to adrenergic receptors should be confirmed to be antagonists by a functional assay, such as adenylyl cyclase activity (see below).

Preferred β-adrenergic receptor antagonists for use in the present invention are those with no or low intrinsic sympathomimetic activity and, preferably, low inverse agonist activity. As used herein, an adrenergic receptor antagonist having low inverse agonist activity has less than about 50% inverse agonist activity, preferably less than about 40% inverse agonist activity, and even more preferably less than about 30% inverse agonist activity. An adrenergic receptor antagonist having low intrinsic sympathomimetic activity has less than about 30% intrinsic sympathomimetic activity, more preferably less than about 20% intrinsic sympathomimetic activity, and even more preferably less than about 10% intrinsic sympathomimetic activity.

Adrenergic receptor antagonists having low intrinsic sympathomimetic activity and low inverse agonist activity may be identified as described in co-pending application Ser. No. 09/047,755, entitled "Method For Identifying Adrenergic Receptor Antagonists Having Good Tolerability," filed Mar. 25, 1998, claiming benefit of provisional application Ser. No. 60/043,906, filed Apr. 3, 1997, the complete disclosures of which are incorporated herein by reference. Briefly, the basal adrenergic receptor signaling activity is measured. The basal signaling activity is the level of measurable intrinsic signaling activity of unoccupied adrenergic receptors) or any defined level of receptor signaling activity, such as the level of activity which is achieved upon stimulation of a particular receptor (e.g., a $\beta_1$-adrenergic receptor) with a specific amount of a known agonist. Adrenergic receptor signaling activity can be quantitated by measuring any cellular response initiated by adrenergic receptor signal transduction. For instance, the adenylyl cyclase activity associated with the adrenergic receptor, the heart contractility support provided by the adrenergic receptor, or the level of phosphorylation of protein kinase A associated with the adrenergic receptor can be measured. Methods of measuring adenylyl cyclase activity, heart contractility support, and level of phosphorylation of protein kinase A are known in the art. See, e.g., Samama et al., *Molec. Pharmacol.*, 45, 390–94 (1994); Chidiac et al., *Molec. Pharmacol.*, 45, 490–99 (1994); Tate et al., *Eur. J. Biochem.*, 196, 357–361 (1991); *Methods In Enzymology*, volume 200, "Protein Phosphorylation, Part A," (Hunter and Lefton eds., 1991). An adrenergic receptor antagonist having inverse agonist activity can be identified, for example, by its ability to decrease adenylyl cyclase activity compared to basal adenylyl cyclase activity, to inhibit heart contractility support by the adrenergic receptor compared to the basal level of heart contractility support, and/or to decrease the level of phosphorylation of protein kinase A associated with the adrenergic receptor compared to the basal level of phosphorylation of protein kinase A. An adrenergic receptor antagonist having intrinsic sympathomimetic activity can be identified, for example, by its ability to increase adenylyl cyclase activity compared to basal adenylyl cyclase activity, to increase heart contractility support provided by the adrenergic receptor compared to the basal level of heart contractility support, and/or to increase the level of phosphorylation of protein kinase A associated with the adrenergic receptor compared to the basal level of phosphorylation of protein kinase A. As can be seen from the above discussion, the basal adrenergic receptor signaling activity, the inverse agonist activity and the intrinsic sympathomimetic activity can all conveniently be measured in a single assay. For instance, adenylyl cyclase activity could be measured. An adrenergic receptor antagonist useful in the present invention would produce no more than about a 50% reduction, and less than about a 30% increase, in adenylyl cyclase activity compared to basal adenylyl cyclase activity.

Adrenergic receptor antagonists having low intrinsic sympathomimetic activity and low inverse agonist activity produce limited adverse side effects in a patient to whom the adrenergic receptor antagonist is administered (i.e., the adrenergic receptor antagonist is well tolerated by the patient). The less the inverse agonist activity and the less the intrinsic sympathomimetic activity, the greater the decrease in adverse side effects. Adverse side effects are undesirable effects or conditions which are directly or indirectly caused by the pharmacological activity of an adrenergic receptor antagonist. These adverse side effects can include bradycardia, myocardial depression, dyspnea, hypotension, congestive heart failure, worsening of asthma, worsening of chronic obstructive pulmonary disease, intermittent claudication, Raynaud's phenomenon, mental depression, increased risk of hypoglycemia (among insulin-dependent diabetic patients), easy fatigability, disturbingly vivid dreams, insomnia, impaired sexual function, or fluid retention. A decrease in such adverse side effects can refer to a decrease in the number of different side effects experienced by a patient, to a decrease in the severity of a particular side effect experienced by a patient, or to a decrease in the occurrence of a particular side effect experienced by a patient.

Preferably, the β-adrenergic antagonist used in the method of the invention is metoprolol, carvedilol or bucindolol. Most preferably, the β-adrenergic antagonist is metoprolol.

Effective dosage forms, modes of administration and dosage amounts of the β-adrenergic antagonist, may be determined empirically, and making such determinations is within the skill of the art. It is understood by those skilled in the art that the dosage amount will vary with the activity of the particular agent employed, the severity of the heart failure, the route of administration, the rate of excretion, the duration of the treatment, the identity of any other drugs being administered to the patient, the age and size of the patient, and like factors well known in the medical art.

Suitable modes of administration can include, but are not limited to, oral, nasal, topical, transdermal, rectal, and parenteral routes. Preferred parenteral routes include, but are not limited to, subcutaneous, intradermal, intravenous, intramuscular and intraperitoneal routes. Preferred is oral administration.

In the method of the invention, administration of a low dose of the β-adrenergic antagonist is begun after the patient receiving the positive inotropic agent is hemodynamically and clinically stable. The amount of the β-adrenergic antagonist is gradually increased until an effective dose is achieved. An effective daily dose of the β-adrenergic antagonist will be that amount of the agent which is the lowest dose effective to produce a therapeutic effect and which maintains the hemodynamic and clinical stability of the patient. A suggested daily dosage of metoprolol is about 100 to 200 mg/day, a suggested daily dosage of carvedilol is about 50 mg/day, and a suggested daily dosage of bucindolol is about 100 mg/day. However, the total daily dosage of these or other β-adrenergic antagonists will be determined by an attending physician within the scope of sound medical judgment. If desired, the effective daily dose may be administered as two, three, four, five, six or more sub-doses, administered separately at appropriate intervals throughout the day.

In general, the "low dose" for beginning administration of the β-adrenergic receptor will be about 5–10% of expected final effective dose. Thus, a suggested low dose of metoprolol is about 5–20 mg/day, a suggested low dose of carvedilol is about 2.5–5.0 mg/day, and a suggested low dose of bucindolol is about 5–10 mg/day.

Treatment with the combination of full effective doses of β-blocker and positive inotrope can be continued indefinitely. Preferably, however, the dose of the positive inotropic agent is gradually reduced to the lowest possible dose that does not lessen the hemodynamic and clinical stability of the patient. If possible, the administration of the positive inotrope is discontinued altogether.

An attempt to reduce the dose of the positive inotrope should not be begun until the patient is stable and, preferably, also exhibits improved myocardial function as assessed by an improved left ventricular ejection fraction. Generally, the positive inotrope and the β-adrenergic antagonist should be administered in combination for at least two months before attempting to reduce the dose of the positive inotrope.

Withdrawal of the positive inotrope is preferably accomplished by decreasing the positive inotropic dose by 50% weekly until the subject is off the drug. If clinical deterioration occurs, which is common, the positive inotropic agent should be returned to the previous dose that was associated with clinical stability.

The majority of patients do better on the combination of a positive inotropic agent and a β-adrenergic antagonist. However, approximately one-third can be weaned from the inotropic agent.

The following experimental results are provided for purposes of illustration and are not intended to limit the scope of the invention.

EXAMPLES

EXAMPLE 1

Treatment of Heart Failure with a Combination of Enoximone and Metoprolol

A. Subject Population

Subjects with end-stage, refractory heart failure from severe systolic dysfunction, on or off intravenous (i.v.) inotropic therapy, who were hospitalized for heart failure decompensation or had recently been hospitalized, were used in the study. Demographic details and baseline data of the study population are given in Table 3. Baseline refers to the status of the subjects prior to beginning the treatment described below.

TABLE 3

Baseline and Demographic Data

| PARAMETER | MEAN BASELINE VALUE ± SEM* |
|---|---|
| 1. Age(years)(n = 30) | 53 ± 2.9 |
| 2. Left Ventricular Ejection Fraction (LVEF)(%)(n + 30) | 17.2 ± 1.2 |
| 3. Heart Rate(beats/min.)(n = 28) | 101 ± 4 |
| 4. New York Heart Assn. 100% Class IV Class(IV/III/II/I)(n = 30) | |
| 5. Gender(M/F)(n = 30) | 22/8 |
| 6. Number of subjects on i.v. inotropes (n = 30) | 18/30 |
| 7. Cardiac index(L/min/m$^2$) (n = 14) | 1.6 ± 0.1 |
| 8. Pulmonary capillary wedge pressure (mmHg)(n = 14) | 25.2 ± 1.5 |
| 9. Etiology of cardiomyopathy | |
| IDC# | 23(77%) |
| Ischemic | 4(13%) |
| Valvular | 2(7%) |
| Anthracycline | 1(3%) |

*SEM = standard error of the mean
IDC = idiopathic dilated cardiomyopathy

B. Treatment

1. Phase 1: Stabilization on an oral dose of a positive inotropic agent. Enoximone, a positive inotropic agent, was administered orally, beginning at doses of 1.0–2.0 mg/kg/day given in 3 or 4 divided doses (e.g. 0.25 mg/kg q.i.d.). As the dose of the oral inotropic agent was being increased, the subject was withdrawn from i.v. inotropic support, if any. The i.v. inotrope was typically the β-adrenergic receptor agonist dobutamine. When the subject was completely off i.v. inotropic support and was hemodynamically and clinically stable (mentating normally and stable and satisfactory renal and pulmonary function), the patient was progressively ambulated and ultimately discharged from the hospital.

2. Phase 2: Adjustment of oral heart failure medication in an outpatient setting. For the next 2–6 weeks oral heart failure medication including diuretics, ACE inhibitors, digoxin and enoximone were adjusted to optimal levels as the patient was progressively physically rehabilitated.

3. Phase 3: Institution of oral β-adrenergic receptor antagonist (β-blocker) therapy. Once the patient was stable, oral administration was begun at a low dose (6.25 mg/day) of the β-adrenergic receptor antagonist metoprolol given in addition to the enoximone. The metoprolol was then up-titrated to a standard effective dose (typically 100–200 mg/day in one, two or three doses per day). Treatment with the combination of full doses of metoprolol and enoximone was continued for 2–4 months.

4. Phase 4: Attempted withdrawal of the positive inotropic agent. In subjects who were stable and had improvment in their myocardial function (LVEF improvement ≧5 EF units), an attempt was made to withdraw the enoximone and continue treatment with metoprolol alone. This was done by decreasing the enoximone dose by 50% weekly until the subject was off the drug. If clinical deterioration occurred, which was common, the enoximone was returned to the previous dose which was associated with clinical stability. The majority of subjects did better on the combination of enoximone and metoprolol, but approximately one-third were weaned from the enoximone.

5. Phase 5: Long term treatment. Treatment with metoprolol alone or the combination of enoximone and metoprolol was continued indefinitely or until cardiac transplantation was possible.

C. Outcome of Treatment.

SAS software (SAS Institute, Cary, N.C.) was used for all statistical analyses. All tests were two-sided and significance level was taken to be 0.05. When appropriate, data are expressed as mean ± standard error of the mean (SEM). Paired data (at baseline and on treatment) were analyzed by the paired t-test or, if the distribution of the paired differences was not normal, by the sign test.

Survival curves and confidence intervals were estimated by the actuarial method. Survival data for patients undergoing transplantation were censored at the time of transplantation. The survival curves from the CONSENSUS and PROMISE trials were estimated from published data [The CONSENSUS Trial Study Group. Results of the Cooperative North Scandinavian Enalapril Survival Study (CONSENSUS). *N. Engl. J. Med.*, 316, 1429–35 (1987); Packer et al., for the PROMISE Study Research Group, *N. Engl. J. Med.*, 325, 1468–75 (1991)]. They were compared to the survival data for patients in the present study using the log rank test (see FIG. 2).

1. Treatment Tolerability

Of the 30 subjects treated in the present study, 29 (96%) tolerated the positive inotropic agent enoximone. All of the 18 subjects who were on i.v. inotropic agents were weaned to oral therapy.

Twenty-four subjects (80%) tolerated the β-blocker metoprolol. Five did not, and one subject underwent cardiac transplantation before β-blocker therapy could be initiated.

Of the 23 subjects treated with the combination of enoximone and metoprolol, 11 (48%) were weaned from the β-blocker, leaving 12 (52%) who were more clinically stable on the combination. The average treatment duration on the combination was 9.4±1.8 months. The mean length of follow-up (until transplantation) was 20.9±3.9 months.

The average dose of enoximone used in these subjects was 189±13 mg/day, and the average dose of metoprolol was 113±9 mg/day.

2. Effects on heart rate and left ventricle (LV) function.

As can be observed in Table 4 below, the combination of a positive inotropic agent and a β-blocker is associated with improved LV function and a marked reduction in heart rate as compared to baseline levels, both favorable effects from the standpoint of predicting subsequent clinical outcome. Both changes were statistically significant.

TABLE 4

Effect on left ventricle function and heart rate

|  | Number Evaluable | Baseline | On Therapy | p |
|---|---|---|---|---|
| LVEF (%)* | 20 | 17.7 ± 1.6 | 27.6 ± 3.4 | 0.01 |
| HR (beats/min) | 26 | 101 ± 4 | 80 ± 4 | 0.0001 |

*LVEF = left ventricle ejection fraction assessed at 16 ± 3 months

3. Effects on heart failure symptoms and hospitalizations

The combination of the positive inotropic agent enoximone and the β-blocking agent metoprolol reduced symptoms as assessed by the New York Heart Association (NYHA) Functional Classification (see Table 5). The combination also tended to reduce hospitalizations in the year after, compared to the year before, initiation of treatment as shown in Table 5.

TABLE 5

Effect on Hospitalizations and HYHA

|  | Number Evaluable | Baseline | On Therapy | p |
|---|---|---|---|---|
| NYHA Class | 30 | 4 ± 0 | 2.8 ± 0.1 | 0.0001 |
| Hospitalizations/Yr | 12 | 2.3 ± 0.3 | 1.0 ± 0.6 | 0.06 |

4. Clinical outcome

The clinical outcome at the time of last follow-up (mean 20.9±3.9 months)for the 30 treated subjects is shown in Table 6.

TABLE 6

Clinical Outcome

|  | Number of Patients (%) |
|---|---|
| Alive Without Transplantation | 15 (50.0) |
| Alive, Transplanted | 9 (30.0) |
| Cardiac Death | 5 (16.7) |
| Noncardiac Death | 1 (3.3) |

5. Comparison To Other Treatments

A comparison of the above results of the present study was made to results obtained using other therapies for late-stage heart failure. In particular, a comparison was made the enalapril-treated class IV patients in the CONSENSUS trial (N. Engl. J. Med. 1987, 316:1429–35) and to the placebo group (standard therapy) class IV patients in the PROMISE trial (N. Engl. J. Med. 1991, 325:1468–75).

Figure 2:
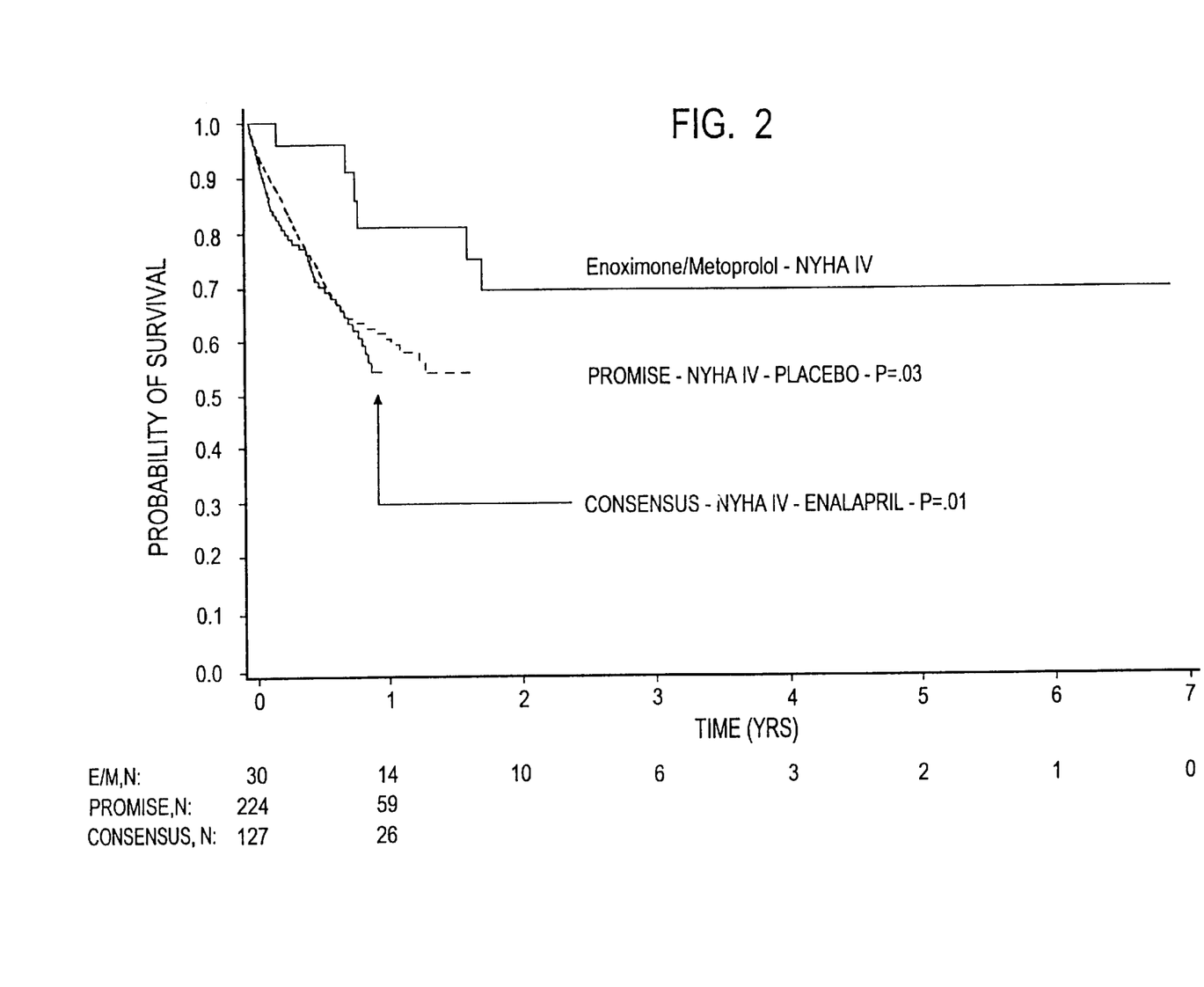
FIG. 2 shows a comparison of the survival function curves of patients treated with enoximone and metoprolol (this study) to New York Heart Association class IV placebo-treated patients in the PROMISE trial and to enalapril-treated patients in the CONSENSUS trial.

Estimated survival rates for patients in the present study were, in percent (95% confidence interval) 96 (88–100) at six months, 81 (64–98) at one year, and 69 (49–90) at two years. These results are significantly better (p=0.01) than for enalapril-treated class IV patients (approximate one-year actuarial survival=54%) in the CONSENSUS trial in which enalapril (an ACE inhibitor) was found significantly better than placebo. Similarly, the results of the present study are significantly better (p=0.03) than for standard-therapy class IV patients (approximate one-year actuarial survival=61%) in the PROMISE trial in which standard therapy was found significantly better than milrinone. FIG. 2 shows estimated survival curves for the three studies.

Four papers were reviewed for another comparison. They were:

1. Baim et al., Evaluation of a New Bipyridine Inotropic Agent—Milrinone—in Patients with Severe Congestive Heart Failure, N Engl J Med, 309, 748–56 (1983).
2. DiBianco et al, A Comparison of Oral Milrinone, Digoxin and Their Combination in the Treatment of Patients with Chronic Heart Failure, N Engl J Med, 320, 677–83 (1989).
3. Packer et al, Effect of Oral Milrinone on Mortality in Severe Chronic Heart Failure, N Engl J Med, 325, 1468–75 (1991).
4. Cowley et al, Treatment of Severe Heart Failure: Quantity or Quality of Life? A Trial of Enoximone, Br Heart J, 72, 226–30 (1994).

A comparison of the results of the studies reported in these four articles with the results of the present study led to the following observations:

a) In the present study, at baseline, NYHA class (mean=4.0) was substantially worse than in the other studies (means=3.4, 2.8, 3.4 and 3.2, respectively).

b) At baseline in the present study, heart rates (mean=101) were substantially worse than in the other studies in which rates were measured (Baim et al. 77 and Packer et al. 84). Rates in the present study improved greatly while those in the Baim et al. study worsened.

c) Rates of hospitalization for patients in the present study tended to improve (2.3 to 1.0 per subject per year). Rates for patients in the Packer et al. and Cowley et al. studies also improved. No rates were given for the other two studies.

d) LVEF in the present study improved substantially, from 18 to 28 (p=0.01), much more than in any of the other studies for which LVEF's were reported.

e) Correcting all studies for median length of follow-up, mortality rates in the present study were less that those in any of the other studies and actuarial survival rates were better than those of any of the other studies, despite the worse baseline status of patients in the present study (see a) above).

EXAMPLE 2

Treatment of Heart Failure with a Combination of Vesnarinone and Metoprolol

Vesnarinone is another positive inotrope, but it has a different mechanism of action than enoximone. In addition to mild phosphodiesterates inhibition, vesnarinone also produces a decrease in potassium currents and increases intracellular sodium by prolonging the opening of sodium channels. See Feldman et al., New Eng. J. Med., 329, 149–155 (1993); Tiara et al., "Model and mechanism of action of 3,4-dihydro-6-[4-(3,4-dimethoxybenzoyl)-1-piperzainyl]-2 (1H)-quinolinone (OPC-8212), a novel positive inotropic drug, on the dog heart," Arzneim-Forsch Drug Res, 34(I):3a, 1984. Eight NYHA Class III-IV heart failure patients were treated with vesnarinone and metoprolol essentially as described in Example 1. Other NYHA Class III–IV heart failure patients from a clinical trial receiving placebo or vesnarinone alone (the VEST trial) were used as controls. The final doses were 60 mg/day placebo (VEST trial), 60 mg/day vesnarinone (VEST trial), and a combination of 60 mg/day vesnarinone and 100 mg/day metoprolol (this study).

Figure 3:
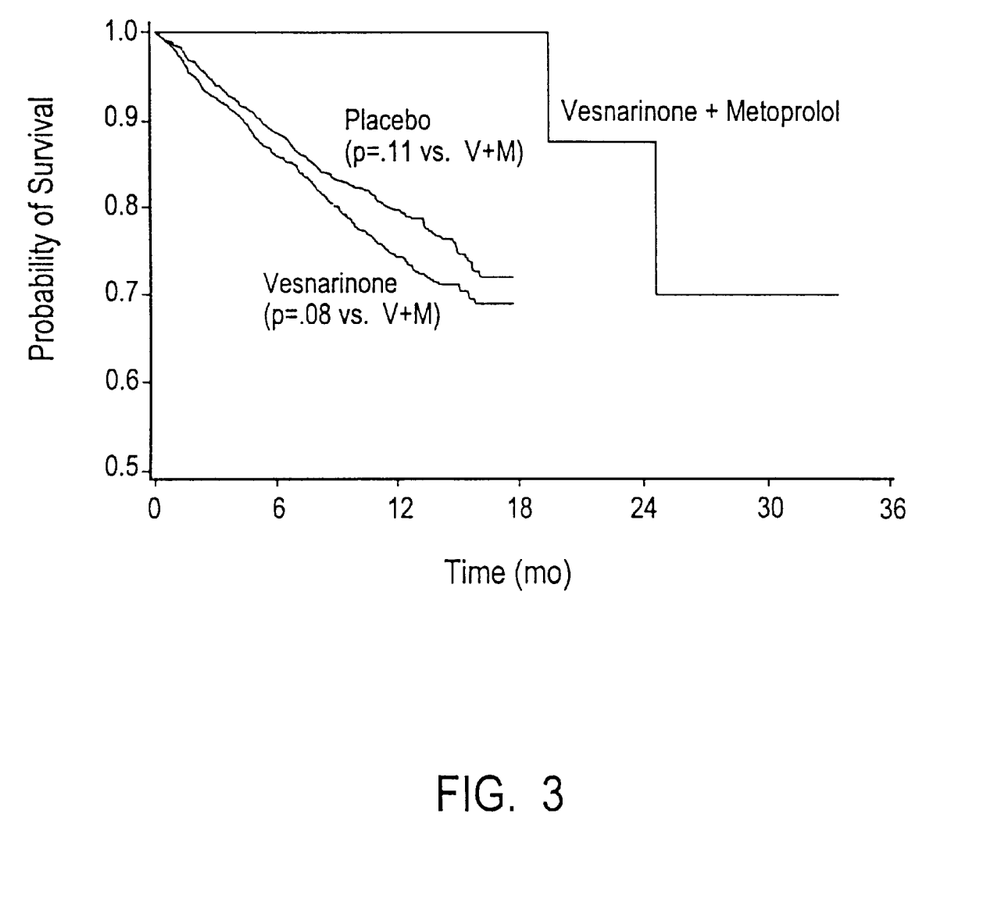
FIG. 3. Graph of time versus probability of survival for NYHA Class III-V heart failure patients treated with placebo, vesnarinone alone, or a combination of vesnarinone and metoprolol.

The results are presented in FIG. 3. As can be observed in FIG. 3, in the VEST trial, vesnarinone treatment was associated with an increase in mortality compared to placebo (p=0.01). However, in subjects treated with vesnarinone and metoprolol, the survival tended to be better (p=0.08 vs. vesnarinone). If 22 subjects, instead of 8, had been treated with the vesnarinone and metoprolol combination, the p value would have been 0.05, indicating that the small sample size precluded the achievement of statistical significance.

Taken together, the data with both enoximone and vesnarinone indicate that the addition of β-blockade to positive inotropic therapy is feasible and results in a reduction in adverse events, including mortality, compared to treatment with a positive inotrope only.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

I claim:

1. A method of treating heart failure comprising:
   administering an effective amount of a positive inotropic agent to a patient suffering from heart failure until the patient is hemodynamically and clinically stable;
   then administering a low dose of a β-adrenergic receptor antagonist to the patient;
   gradually increasing the dose of the β-adrenergic receptor antagonist to an effective dose; and
   continuing to administer effective doses of both the positive inotropic agent and the β-adrenergic receptor antagonist.

2. The method of claim 1 wherein the positive inotropic agent is administered orally.

3. The method of claim 1 wherein the positive inotropic agent is enoximone.

4. The method of claim 3 wherein the enoximone is administered orally.

5. The method of claim 4 wherein the enoximone is administered at a dose of about 1–3 mg/kg/day given in 3–4 doses per day.

6. The method of claim 1 wherein the β-adrenergic receptor antagonist is administered orally.

7. The method of claim 1 wherein the β-adrenergic receptor antagonist is metoprolol.

8. The method of claim 7 wherein the metoprolol is administered orally.

9. The method of claim 8 wherein the low dose of metoprolol is about 5–10 mg/day and the effective dose of metoprolol is about 100 to 200 mg/day.

10. The method of claim 3 wherein the β-adrenergic receptor antagonist is metoprolol.

11. The method of claim 10 wherein the enoximone and metoprolol are administered orally.

12. The method of claim 11 wherein the enoximone is administered at a dose of about 1–3 mg/kg/day given in 3–4 doses per day, and the low dose of metoprolol is about 5–10 mg/day and the effective dose of metoprolol is about 100 to 200 mg/day.

13. The method of claim 1 wherein the heart failure is advanced, late-stage chronic heart failure.

14. The method of claim 1 further comprising, after the positive inotropic agent and the β-adrenergic receptor antagonist have been administered in combination for at least two months, gradually reducing the dose of the positive inotropic agent to the lowest possible dose that does not reduce the hemodynamic and clinical stability of the patient.

15. The method of claim 14 wherein the use of the positive inotropic agent is discontinued.

* * * * *